(12) United States Patent
Machhammer et al.

(10) Patent No.: US 6,413,379 B1
(45) Date of Patent: *Jul. 2, 2002

(54) CONTINUOUS RECOVERY OF (METH) ACRYLIC ACID

(75) Inventors: Otto Machhammer, Mannheim; Susanne Haupt, Offenbach; Volker Schliephake, Schifferstadt; Jürgen Schröder, Ludwigshafen, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/362,911

(22) Filed: Jul. 29, 1999

(30) Foreign Application Priority Data

Aug. 26, 1998 (DE) .......................... 198 38 783

(51) Int. Cl.$^7$ ............................ B01D 3/34; C07C 51/44
(52) U.S. Cl. ................... 203/49; 203/80; 203/DIG. 21; 562/600
(58) Field of Search ...................... 203/29, 49, DIG. 21, 203/73, 80; 562/600

(56) References Cited

U.S. PATENT DOCUMENTS

| | | | |
|---|---|---|---|
| 3,932,500 A | | 1/1976 | Duembgen et al. |
| 4,142,058 A | * | 2/1979 | Matsumura et al. ........ 562/600 |
| 4,199,410 A | * | 4/1980 | Ohrui et al. ................... 203/73 |
| 4,219,389 A | * | 8/1980 | Brink et al. .................... 203/72 |
| 5,183,539 A | * | 2/1993 | Honma et al. ................. 203/49 |
| 5,426,221 A | | 6/1995 | Willersinn |
| 5,637,222 A | * | 6/1997 | Herbst et al. ............... 210/634 |
| 5,855,743 A | | 1/1999 | Herbst et al. |
| 5,897,749 A | * | 4/1999 | Kroker et al. ....... 203/DIG. 21 |
| 5,961,790 A | * | 10/1999 | Herbst et al. ........ 203/DIG. 21 |

FOREIGN PATENT DOCUMENTS

| | | |
|---|---|---|
| DE | 21 36 396 | 2/1973 |
| DE | 28 34 140 | 8/1978 |
| DE | 43 08 087 | 9/1994 |
| DE | 197 46 690 A 1 | 10/1997 |
| EP | 0 722 926 A1 | 7/1996 |

OTHER PUBLICATIONS

Ullmann's Encylopedia, 4$^{th}$ Edition, Band 7, page 81.

* cited by examiner

Primary Examiner—Virginia Manoharan
(74) Attorney, Agent, or Firm—Oblon, Spivak, McClelland, Maier & Neustadt, P.C.

(57) ABSTRACT

A process for the continuous recovery of (meth)acrylic acid from a liquid starting mixture containing (meth)acrylic acid, a high-boiling organic solvent and low boilers, medium boilers and high boilers is proposed, the mixture being separated into a first part-stream (a), which, in addition to (meth)acrylic acid, contains the low boilers and a part each of the medium boilers and high boilers, and a second part-stream (b), which contains the predominant part of the (meth)acrylic acid and is completely or virtually completely free of low boilers, and the (meth)acrylic acid being recovered from the part-stream (b).

9 Claims, 2 Drawing Sheets

CONTINUOUS RECOVERY OF (METH) ACRYLIC ACID

BACKGROUND OF THE INVENTION

1. Field of the Invention

Figure 1:
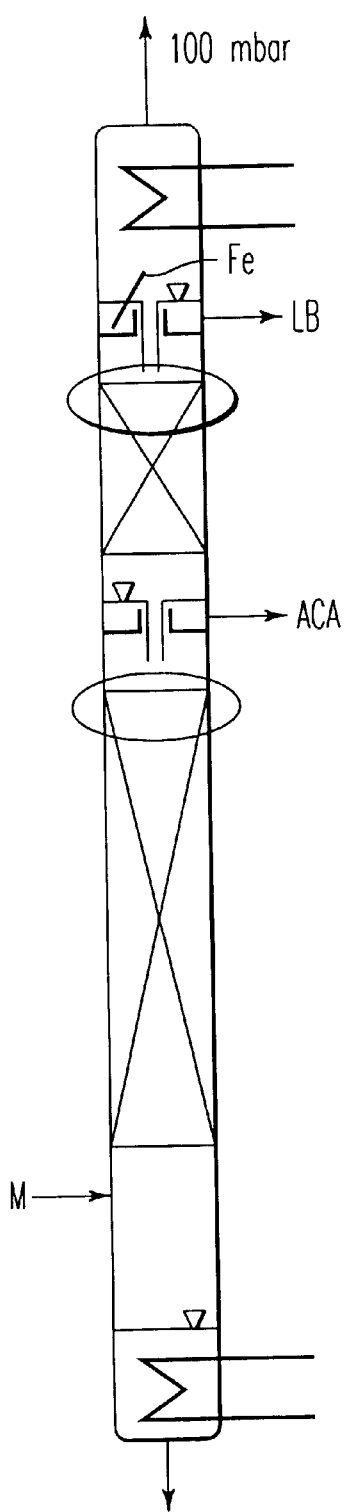

The present invention relates to a process for the continuous recovery of (meth)acrylic acid by absorption of (meth)acrylic acid from the reaction gases of a catalytic gas-phase oxidation. Below, the term (meth)acrylic acid represents the substances acrylic acid and/or methacrylic acid.

2. Discussion of the Background (Meth)acrylic acid is prepared predominantly by catalytic gas-phase oxidation of suitable starting materials, in particular of propene and/or acrolein in the case of acrylic acid or of isobutene and/or methacrolein in the case of methacrylic acid.

A number of possibilities are known for isolating the (meth)acrylic acid from the reaction gases of the catalytic gas-phase oxidation, including isolation by absorption into a solvent.

DE-B 21 36 396 discloses that acrylic acid can be isolated from the reaction gases obtained in the catalytic oxidation of propene or acrolein by countercurrent absorption of the mixture of 75% by weight of diphenyl ether and 25% by weight of biphenyl. Furthermore, DE-A 24 49 780 discloses the cooling of the hot reaction gas by partial evaporation of the solvent in a direct condenser (quench apparatus) before the countercurrent absorption. The problem here and in further process steps, in particular in the purification of the (meth)acrylic acid by distillation, is the production of solids in the apparatuses, which reduces the availability of the plant. According to DE-A 43 08 087, this production of solids can be reduced in the case of acrylic acid by adding a polar solvent, such as dimethyl phthalate, in an amount of from 0.1 to 25% by weight, to the relatively nonpolar solvent mixture comprising diphenyl ether and biphenyl; as a result, the absorptivity of the solvent mixture for the dirt-forming substances increases. With increasing polarity, however, the solvent absorbs increasing amounts of water; furthermore, this leads to greater solvent losses via the dilute acid solution.

In the presence of solvents, at elevated temperatures as occur in the recovery of (meth)acrylic acid by the process of the generic type, in particular at the lowermost collecting tray of the absorption column, in the stripping and bottom section of the distillation column and in the heat exchangers, the polyacrylic acid forms a dirt which adheres firmly to the surface of the apparatuses and can be detached only with alkalis. Analyses have shown that the dirt consists of a mixture of from about 10 to 50% by weight of poly(meth)acrylic acid, the remainder being solvent.

It has long been presumed that the tendency of (meth)acrylic acid to polymerization is promoted by low boilers.

The addition of polymerization inhibitors is described, for example, in Ullmanns Encyklopädie der techn. Chemie, 4th Edition, Vol. 7, page 81, left column. The inhibitors proposed in particular are phenothiazine or hydroquinone in minimum amounts of 500 ppm, but they have the disadvantage that they are expensive and furthermore cannot effect complete inhibition.

SUMMARY OF THE INVENTION

It is an object of the present invention to reduce the tendency of (meth)acrylic acid to polymerize in a process for the continuous recovery of (meth)acrylic acid from a liquid mixture with a high-boiling solvent and with low boilers, medium boilers and high boilers.

We have found that this object is achieved by a process for the continuous recovery of (meth)acrylic acid from a liquid starting mixture containing (meth)acrylic acid, a high-boiling organic solvent and low-boilers, medium boilers and high boilers. In the invention, I the mixture is separated into a first part-stream (a), which, in addition to (meth)acrylic acid, contains the low boilers and a part of, in each case, the medium boilers and high boilers, and a second part-stream (b), which contains the predominant part of the (meth)acrylic acid and is completely or virtually completely free of low boilers, and II the (meth)acrylic acid is recovered from the part-stream (b).

DETAILED DESCRIPTION OF THE INVENTION

We have found that the action of low boilers which promotes the polymerization of (meth)acrylic acid at elevated temperatures can be reduced in a surprising manner if the low boilers are separated off in the presence of the high boilers.

Here, solvents whose boiling point is higher than the boiling point of the respective desired main product (about 141° C. for acrylic acid or about 161° C. for methacrylic acid, in each case at atmospheric pressure) are defined as being high-boiling.

Starting mixtures for the present process are the reaction gases from the catalytic gas-phase oxidation of $C_3$-alkanes, $C_3$-alkenes, $C_3$-alkanols and/or $C_3$-alkanals or intermediates thereof to give acrylic acid or of $C_4$-alkanes, $C_3$-alkanes, $C_3$-alkenes, $C_3$-alkanols and/or $C_3$-alkanals or intermediates thereof to give (meth)acrylic acid. The process is described below for acrylic acid but also applies in an analogous manner for methacrylic acid.

The catalytic gas-phase oxidation of propene and/or acrolein to acrylic acid with air or molecular oxygen by known processes, in particular as described in the above mentioned publications, is particularly advantageous. Temperatures of from 200 to 450° C. and, if required, superatmospheric pressure are preferably used here. Preferably used heterogeneous catalysts are oxidic multicomponent catalysts based on the oxides of molybdenum, bismuth and iron in the 1st stage (oxidation of propene to acrolein) and on the oxides of molybdenum and vanadium in the 2nd stage (oxidation of acrolein to acrylic acid). If propane is used as a starting material, it can be converted into a propene/propane mixture by catalytic oxydehydrogenation, as described in U.S. Pat. No. 5,510,558, or by homogeneous oxydehydrogenation, as described, for example, in CN-A-1 105 352, or by catalytic dehydrogenation, according to the Example of EP-A-0 253 409. When a propene/propane mixture is used, propane acts as a diluent gas. Other suitable propene/propane mixtures are refinery propene (70% of propene and 30% of propane) or cracker propene (95% of propene and 5% of propane). In principle, propene/propane mixtures such as the above mentioned ones can be oxidized with oxygen or air or a mixture of oxygen and nitrogen of any composition to give acrolein and acrylic acid.

The conversion of propene into acrylic acid is highly exothermic. The reaction gas which, in addition to the starting materials and products, advantageously contains an inert diluent gas, for example recycled gas (cf. below), atmospheric nitrogen, one or more saturated $C_1$- to $C_6$-hydrocarbons, in particular methane and/or propane, and/or steam, can therefore absorb only a small part of the heat of reaction. Although the type of reactors used is not subject to any restriction per se, tube-bundle heat exchangers which are cooled by means of a salt bath and are filled with the oxidation catalyst are generally used since in these heat exchangers the heat evolved in the reaction can be very readily removed by convection and radiation to the cooled tube walls.

The catalytic gas-phase oxidation gives not pure acrylic acid but a gaseous mixture which, in addition to the acrylic acid, may contain, as secondary components, essentially unconverted acrolein and/or propene, steam, carbon monoxide, carbon dioxide, nitrogen, propane, oxygen, acetic acid, propionic acid, formaldehyde, further acids and aldehydes and maleic anhydride. Usually, the reaction product mixture contains, based in each case on the total reaction mixture, from 1 to 30% by weight of acrylic acid, from 0.05 to 1% by weight of propene and from 0.05 to 1% by weight of acrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of the sum of maleic acid and maleic anhydride and from 20 to 98, preferably from 50 to 98, % by weight of inert diluent gases. In particular, saturated $C_1$–$C_6$-hydrocarbons, such as from 0 to 5% by weight of methane and/or propane, as well as from 1 to 30% by weight of steam, from 0.05 to 15% by weight of carbon oxides and from 0 to 90% by weight of nitrogen, based in each case on 100% by weight of reaction gas, are present as inert diluent gases.

The acrylic acid and a part of the secondary components are separated from the reaction gas of the catalytic gas-phase oxidation by absorption in a high-boiling solvent. Preferably, the boiling point of the high-boiling solvent is at least 20° C., in particular 50° C., or more preferably 70° C., above the boiling point of acrylic acid or methacrylic acid. Preferred solvents, the term solvent including solvent mixtures in the present application, have boiling points (at atmospheric pressure) of from 180 to 400° C., in particular from 220 to 360° C. Suitable solvents are high-boiling, extremely hydrophobic solvents which contain no externally acting polar groups, such as aliphatic or aromatic hydrocarbons, for example middle oil fractions from paraffin distillation, or ethers having bulky groups on the oxygen atom, or mixtures thereof, a polar solvent, such as the 1,2-dimethyl phthalate disclosed in DE-A-43 08 087, advantageously being added to these. Also suitable are esters of benzoic acid and phthalic acid with straight-chain alkanols of 1 to 8 carbon atoms, such as n-butyl benzoate, methyl benzoate, ethyl benzoate, dimethyl phthalate and diethyl phthalate, and thermal oils, such as biphenyl, diphenyl ether and mixtures of biphenyl and diphenyl ether or their chlorine derivatives and triarylalkanes, e.g. 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers.

A particularly preferred solvent is a solvent mixture comprising biphenyl and diphenyl ether, preferably in the azeotropic composition, in particular comprising about 25% by weight of biphenyl and about 75% by weight of diphenyl ether, based on 100% by weight of biphenyl and diphenyl ether, for example the commercially available Diphyl®. Preferably, this solvent mixture contains a polar solvent, such as dimethyl phthalate, in an amount of from 0.1 to 25% by weight, based on the total solvent mixture. This reduces the susceptibility of the plants to soiling.

Here, the terms high boilers, medium boilers and low boilers and corresponding adjectival terms denote compounds which have a higher boiling point than acrylic acid (high boilers) or those which have about the same boiling point as acrylic acid (medium boilers) or those which have a lower boiling point than acrylic acid (low boilers).

Advantageously, the hot reaction gas is cooled before the absorption by partial evaporation of the solvent in a direct condenser or quench apparatus. Venturi scrubbers, bubble columns or spray condensers are particularly suitable for this purpose. The high-boiling secondary components of the reaction gas condense into the unevaporated solvent. In addition, the partial evaporation of the solvent is a purification step for the solvent. In a preferred embodiment of the invention, a part-stream of the unevaporated solvent, preferably from 1 to 10% of the mass flow fed to the absorption column, is taken off and is subjected to solvent purification. Here, the solvent is distilled over and the high-boiling secondary components remain behind and—if necessary after further thickening—can be disposed of, for example incinerated. This solvent distillation serves for avoiding an excessively high concentration of high boilers in the solvent stream. The solvent which has distilled over is preferably fed to the laden solvent stream from the absorption column.

The absorption is carried out in a countercurrent absorption column which is preferably equipped with dual-flow trays or valve trays and to which the solvent is fed from above. The gaseous reaction product and any vaporized solvent from the quench apparatus are passed from below into the column and then cooled to absorption temperature. The cooling is advantageously effected by cooling circulations, i.e. heated solvent is removed from the column, cooled in heat exchangers and recycled to a point above the take-off point of the column. After the absorption, all high boilers, the major part of the acrylic acid and a part of the low boilers are present in the solvent.

The remaining, unabsorbed reaction gas is further cooled in order to separate the condensable part of the low-boiling secondary components, in particular water, formaldehyde and acetic acid, from said reaction gas by condensation. This condensate is referred to below as dilute acid solution. The remaining gas stream consists predominantly of nitrogen, carbon oxides and unconverted starting materials. Some of said gas stream is preferably recycled as diluent gas, referred to below as recycled gas, to the reaction stages. The atmospheric nitrogen and a part of the uncondensed secondary components are removed as waste gas and preferably incinerated.

The absorbate, a liquid mixture of acrylic acid, low boilers, medium boilers and high boilers in a high-boiling solvent, is the starting mixture for stage I of the novel process. The absorbate can, if required, be concentrated, in particular by partial evaporation, before being fed into stage I, initially for increasing the acrylic acid content.

Stage I

The starting mixture contains, as a rule, from 10 to 95, preferably from 77 to 90, % by weight of (meth)acrylic acid, from 5 to 40, preferably from 9 to 20, % by weight of high-boiling solvent and from 0.5 to 5, in particular from 1 to 3, % by weight of the sum of low boilers, medium boilers and high boilers. It is preferably fed to the uppermost column tray of a stripping column operating with distillation. The stripping column can in principle have any type of baffles providing efficient separation, preferably dual-flow or valve trays, but also dumped or stacked packings. The stripping column has a bottom evaporator and, if required, a condenser at the top the column.

The liquid stream to be separated off runs downward through the column and the vapor, predominantly acrylic acid vapor, ascends in the opposite direction from the bottom upward and thus strips the low boilers from the liquid, so that the liquid stream (b) arriving at the bottom is virtually free of low boilers. During the stripping, on the other hand, the medium boilers and high boilers predominantly remain in the liquid and reduce the tendency of the acrylic acid to polymerize during the stripping process.

The vapor stream at the top of the column (part-stream a) is preferably condensed and is recirculated to the absorption stage or to the direct condenser, into the high-boiling solvent. However, it is also possible to feed the vapor stream in vapor form, if necessary after compression, to the absorption stage.

The preferred operating parameters in the stripping column are: top pressure <200, in particular <100, particularly preferably <50, mbar, bottom temperature <140° C., in particular <120° C., particularly preferably <100° C., and acrylic acid concentration in the bottom from 5 to 15, particularly preferably from 8 to 12, % by weight.

It is also possible to carry out process stage I by stripping with inert gas.

Stage II

The acrylic acid is preferably recovered from part-stream b by separating the part-stream b into a first part-stream which contains crude acrylic acid and, if required, may be further purified and a part-stream c. Process stage II is preferably effected by distillation in an ascending stripping column.

Preferably, the descending stripping column for process stage I and the ascending stripping column for process stage II have a common bottom. The part-stream b obtained as a result of process stage I in the common sump of descending and ascending stripping column is separated in the ascending stripping column in process stage II. A part-stream c which predominantly contains the solvent and which, if required after purification, in particular by evaporation in a quench, is recirculated to the absorption stage is obtained in the bottom of the column. In the ascending stripping column, the vapor completely or virtually completely free of low boilers ascends, the medium boilers and high boilers being washed out of the vapor by the liquid reflux. At the top of the column, the vapor is condensed, a part is taken off at the top as product and the remainder is liquid reflux. The product is acrylic acid which is substantially free of low boilers, medium boilers and high boilers.

The invention is explained in more detail below with reference to a drawing and embodiments.

Figure 2:
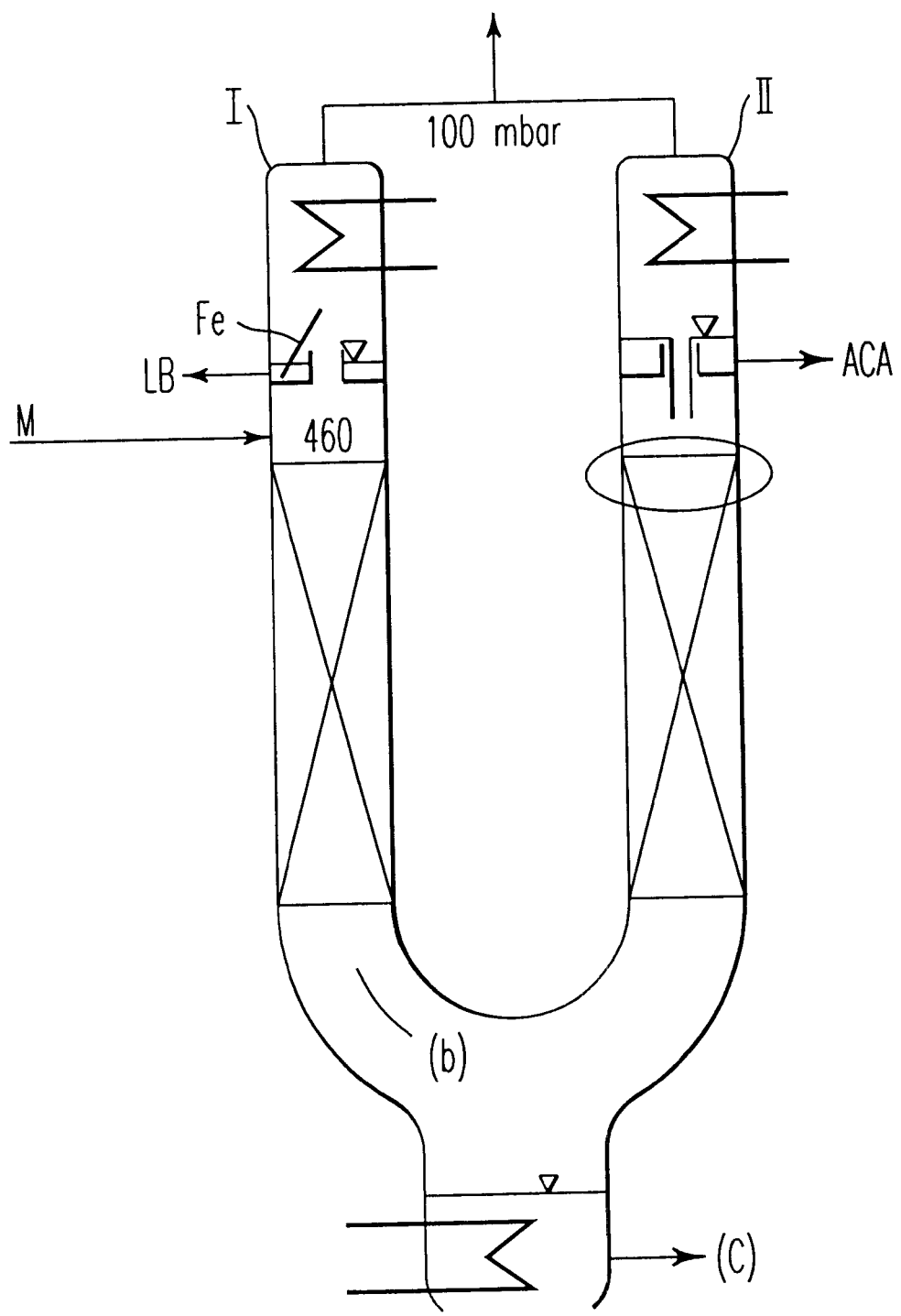

FIG. 1 shows a schematic view of a process for the continuous recovery of acrylic acid from a liquid mixture with a high-boiling solvent and with low boilers, medium boilers and high boilers according to the prior art, FIG. 2 shows a schematic view of a process for the continuous recovery of acrylic acid from a liquid mixture with a high-boiling solvent and with low boilers, medium boilers and high boilers according to the invention.

In the conventional process (FIG. 1), the liquid mixture (M) which, in addition to acrylic acid, contains low boilers, medium boilers and high boilers in a high-boiling solvent is fed to the lower part of a distillation column. A mixture which predominantly contains the solvent and high boilers and medium boilers is taken off from the bottom of the column. The vapor stream, which predominantly contains acrylic acid and the low boilers, ascends and the low boilers (LB) are obtained at the top of the column and the acrylic acid (ACA) is recovered via a side take-off. Since the high boilers and medium boilers are completely or virtually completely removed from the bottom, the liquid reflux in the column contains virtually no high boilers and medium boilers.

In contrast, FIG. 2 schematically shows a process according to the invention: the same liquid starting mixture, which contains acrylic acid as well as low boilers, medium boilers and high boilers in a high-boiling solvent (M), is fed to the top of a descending stripping column I which is equipped with a bottom evaporator and, if required, a condenser at the top. At the top of column I, a part-stream a containing the low boilers (LB) is taken off while the part-stream b is obtained in the bottom of the column and is subsequently separated, in the ascending stripping column II, into a part-stream c which is taken off from the bottom and a part-stream, which contains the acrylic acid (ACA) at the top of the column. Descending stripping column I and ascending stripping column II are equipped with a common bottom.

EXAMPLES

The effect of the separation sequence on the tendency of acrylic acid to polymerize is explained in detail below with reference to examples. For comparison, the same liquid starting mixture was fed in each case to a conventional distillation column and to an apparatus comprising descending stripping column I, ascending stripping column II and common bottom according to the invention. The columns each had a diameter of 30 mm. To shorten the duration of the experiment, sheet iron, which is a strong polymerization promoter, was used in some Examples.

The liquid mixture (M) to be separated had the same composition in all Examples, with the following main components (in each case in % by weight):

61.92 of diphyl
17.32 of acrylic acid
15.50 of dimethyl phthalate
1.72 of diacrylic acid
0.80 of benzoic acid
0.21 of water
0.11 of benzaldehyde
0.04 of acetic acid
0.006 of 2-furaldehyde
0.001 of allyl acrylate

Example 1

The liquid mixture (M) to be separated and having the composition shown above was fed in each case to a column according to the prior art (FIG. 1) and to an apparatus comprising descending stripping column, ascending stripping column and common bottom according to the invention (FIG. 2), with sheet iron as polymerization promoter and without baffles (packings) having a separating effect. The separation quality was poor. With a duration of the experiment of 280 min, polymerization took place neither at the product take-off (ACA) nor at the low boiler take-off (LB) in the conventional process as well as in the process according to the invention.

Example 2

The experimental conditions differed from Example 1 in that no polymerization promoter (sheet iron) was used but baffles which had a separation effect were used in the form of glass rings of 8 mm diameter. A moderate separation quality was achieved. In an experiment lasting 140 minutes, no polymerization was observed at the product take-off in the process according to the prior art, but polymerization was observed after 125 minutes at the low boiler take-off On the other hand, polymerization was observed neither at the product take-off nor at the low boiler take-off in the novel process during an experiment lasting 140 minutes.

Example 3

The experimental conditions differed from the conditions of Example 2 in that glass rings having a smaller diameter (5 mm) and hence a better separation effect were used. In an experiment lasting 120 minutes, no polymerization was observed at the product take-off in the process according to the prior art, but polymerization was observed at the low boiler take-off after 105 minutes. In the process according to the invention, no polymerization took place during an experiment lasting 120 minutes.

Example 4

The experimental conditions corresponded to Example 3, except for the use of glass rings having a smaller diameter of 3 mm as packings with very good separation quality. In the prior art process, polymerization was observed at the product take-off after 48 minutes and at the low boiler take-off after 70 minutes. On the other hand, no polymerization took place in the process according to the invention during an experiment lasting 90 minutes.

Example 5

The packing material differed from that of Example 2, 5 mm metal coils of V2A stainless steel which had very good separation quality being used. In the prior art process, polymerization was observed at the product take-off after 35 minutes but no polymerization was observed at the low boiler take-off during an experiment lasting 90 minutes. In the novel process, on the other hand, polymerization did not begin at the product take-off until after 65 minutes, and no polymerization took place at the low boiler take-off during an experiment lasting 90 minutes.

Example 6

The experimental conditions corresponded to Example 5. In addition, sheet iron was used as a polymerization promoter. In the prior art process, polymerization was observed at the product take-off after only 5 minutes and at the low boiler take-off after 25 minutes. In the novel process, on the other hand, polymerization did not take place at the product take-off until after 15 minutes and no polymerization took place at the low boiler take-off during an experiment lasting 45 minutes.

The experimental results are summarized in Table 1 below:

TABLE 1

| | | Packing | | | Polymerization times | | | |
| | | | | | Comparison | | According to the invention | |
| Example | Polymerization promoter | Size | Material | Separation quality | Product take-off | Low boiler take-off | Product take-off | Low boiler take-off |
| 1 | Sheet iron | none | none | poor | >280 min | >280 min | >280 min | >280 min |
| 2 | none | 8 mm | glass | moderate | >140 min | 125 min | >140 min | >140 min |
| 3 | none | 5 mm | glass | good | >120 min | 105 min | >120 min | >120 min |
| 4 | none | 3 mm | glass | very good | 48 min | 70 min | >90 min | >90 min |
| 5 | none | 5 mm | V2A stainless steel | very good | 35 min | >90 min | 65 min | >90 min |
| 6 | Sheet iron | 5 mm | V2A stainless steel | very good | 5 min | 25 min | 15 min | >45 min |

The composition of the streams at the low boiler take-off (LB) and the product take-off (ACA), in each case for the prior art process and the process according to the invention, which in particular illustrates the respective separation quality achieved, is shown in Table 2 below:

TABLE 2

| | | Comparison | | According to the invention | |
| Example No. | | Low boiler take-off (LB) | Product take-off (ACA) | Low boiler take-off (LB) | Product take-off (ACA) |
| 1 | Acrolein | 0.002% | <0.001% | 0.002% | 0.001% |
| | Water | 1.43% | 0.08% | 1.84% | 0.12% |
| | Acetic acid | 0.32% | 0.13% | 0.29% | 0.24% |
| | Allyl acrylate | 0.01% | 0.005% | 0.OO8% | 0.009% |
| | Propionic acid | 0.025% | 0.022% | 0.022% | 0.025% |
| | Acrylic acid | 94.40% | 81.25% | 84.65% | 93.09% |
| | 2-Furaldehyde | 0.018% | 0.027% | 0.020% | 0.020% |
| | 3-Furaldehyde | 0.005% | 0.006% | 0.005% | 0.006% |
| | Benzaldehyde | 0.12% | 0.28% | 0.180/o | 0.16% |
| | Diacrylic acid | 0.10% | 0.56% | 0.53% | 0.17% |
| | Diphyl | 3.07% | 15.41% | #1.O1% | 5.36% |
| 2 | Acrolein | 0.003% | <0.001% | 0.004% | 0.001% |

TABLE 2-continued

| | | Comparison | | According to the invention | |
|---|---|---|---|---|---|
| Example No. | Low boiler take-off (LB) | | Product take-off (ACA) | Low boiler take-off (LB) | Product take-off (ACA) |
| | Water | 1.82% | 0.07% | 2.40% | 0.15% |
| | Acetic acid | 0.41% | 0.15% | 0.43% | 0.29% |
| | Allyl acrylate | 0.013% | 0.005% | 0.011% | 0.012% |
| | Propionic acid | 0.024% | 0.025% | 0.023% | 0.024% |
| | Acrylic acid | 97.68% | 99.55% | 95.11% | 99.43% |
| | 2-Furaldehyde | 0.007% | 0.019% | 0.012% | 0.010% |
| | 3-Furaldehyde | 0.002% | 0.003% | 0.002% | 0.002% |
| | Benzaldehyde | 0.013% | 0.075% | 0.068% | 0.030% |
| | Diacrylic acid | <0.001% | 0.018% | 0.034% | 0.010% |
| | Diphyl | 0.001% | 0.057% | 1.84% | 0.02% |
| 3 | Acrolein | 0.004% | <0.001% | 0.002% | 0.001% |
| | Water | 5.28% | 0.09% | 3.66% | 0.28% |
| | Acetic acid | 0.56% | 0.15% | 0.46% | 0.164% |
| | Allyl acrylate | 0.019% | 0.005% | 0.012% | 0.008% |
| | Propionic acid | 0.022% | 0.024% | 0.024% | 0.025% |
| | Acrylic acid | 94.07% | 99.60% | 95.64% | 99.41% |
| | 2-Furaldehyde | 0.005% | 0.016% | 0.012% | 0.016% |
| | 3-Furaldehyde | 0.002% | 0.004% | 0.003% | 0.004% |
| | Benzaldehyde | 0.008% | 0.062% | 0.072% | 0.056% |
| | Diacrylic acid | <0.001% | 0.012% | 0.042 | 0.012% |
| | Diphyl | <0.001% | 0.003% | — | 0.014% |
| 4 | Acrolein | 0.004% | <0.001% | 0.003% | 0.001% |
| | Water | 4.87% | 0.17% | 3.11% | 0.35% |
| | Acetic acid | 0.53% | 0.14% | 0.51% | 0.19% |
| | Allyl acrylate | 0.017% | 0.004% | 0.014% | 0.009% |
| | Propionic acid | 0.024% | 0.026% | 0.024% | 0.024% |
| | Acrylic acid | 94.31% | 99.56% | 96.16% | 99.24% |
| | 2-Furaldehyde | 0.003% | 0.015% | 0.011% | 0.008% |
| | 3-Furaldehyde | 0.001% | 0.005% | 0.003% | 0.003% |
| | Benzaldehyde | 0.001% | 0.03% | 0.061% | 0.014% |
| | Diacrylic acid | <0.001% | 0.026% | 0.028% | 0.012% |
| | Diphyl | 0.001% | <0.001% | — | <0.001% |
| 5 | Acrolein | 0.005% | 0.001% | 0.002% | 0.001% |
| | Water | 12.49% | 0.47% | 6.41% | 0.36% |
| | Acetic acid | 1.49% | 0.17% | 0.70% | 0.12% |
| | Allyl acrylate | 0.05% | 0.006% | 0.018% | 0.007% |
| | Propionic acid | 0.025% | 0.026% | 0.024% | 0.025% |
| | Acrylic acid | 85.90% | 99.30% | 90.79% | 99.46% |
| | 2-Furaldehyde | <0.001% | 0.005% | 0.009% | 0.007% |
| | 3-Furaldehyde | <0.001% | 0.003% | 0.003% | 0.002% |
| | Benzaldehyde | 0.021% | 0.002% | 0.058% | 0.007% |
| | Diacrylic acid | <0.001% | 0.017% | 0.032% | 0.013% |
| | Diphyl | 0.02% | 0.002% | 1.94% | 0.001% |

What is claimed is:

1. A process for the continuous recovery of (meth)acrylic acid from a liquid starting mixture containing (meth)acrylic acid, a high-boiling organic solvent, low boilers, medium boilers and high boilers, comprising:

separating said liquid starting mixture into a part-stream (a) and a part-stream (b) in a process stage (I) by distillation in a descending stripping column; wherein said part-stream (a) contains (meth)acrylic acid, the low boilers, a part of the medium boilers and a part of high boilers; and wherein said part-stream (b) contains the predominant part of said (meth)acrylic acid and is completely or virtually completely free of low boilers; and recovering the (meth)acrylic acid from said part-stream (b) as the part-stream (b) is distilled in an ascending stripping column in a process stage (II).

2. The process as claimed in claim 1, wherein said liquid starting mixture contains from 10 to 95% by weight of said (meth)acrylic acid, from 5 to 40% by weight of said high-boiling solvent and from 0.5 to 5% by weight of the sum of low boilers, medium boilers and high boilers.

3. The process as claimed in claim 1, wherein said liquid starting mixture contains from 77 to 90% by weight of (meth)acrylic acid, from 9 to 20% by weight of said high-boiling solvent and from 1 to 3% by weight of the sum of low boilers, medium boilers and high boilers.

4. The process as claimed in claim 1, wherein said descending stripping column has a top pressure of <200 mbar, a bottom temperature of <140° C., and an acrylic acid concentration in the bottom of from 5 to 15% by weight.

5. The process as claimed in claim 1, wherein said descending stripping column has a top pressure of <100 mbar, a bottom temperature of <120° C. and an acrylic acid concentration in the bottom of from 8 to 12% by weight.

6. The process as claimed in claim 1, wherein said process stage (I) is carried out by stripping with inert gas.

7. The process as claimed in claim 1, wherein said part-stream (b) is separated into a first part-stream and a part-stream (c) during said process stage (II);

wherein said first-part stream contains (meth)acrylic acid.

8. The process as claimed in claim 1, wherein the descending stripping column for said process stage (I) and the ascending stripping column for said process stage (II) have a common bottom.

9. The process as claimed in claim 7, wherein said part-stream (c) contains the high-boiling solvent.

* * * * *